United States Patent [19]

Müller et al.

[11] 4,130,650
[45] Dec. 19, 1978

[54] ANTIARRHYTHMIC METHOD OF USE

[75] Inventors: Erich Müller; Willi Diederen, both of Biberach, Germany; Robin G. Shanks, Belfast, Northern Ireland

[73] Assignee: Boehringer Ingelheim GmbH, Ingelheim am Rhein, Germany

[21] Appl. No.: 800,309

[22] Filed: May 25, 1977

[30] Foreign Application Priority Data

Jun. 3, 1976 [DE] Fed. Rep. of Germany ....... 2624918

[51] Int. Cl.² ............................................. A61K 31/44
[52] U.S. Cl. ............................. 424/263; 424/248.58; 424/258; 424/272; 424/273 R; 424/330
[58] Field of Search .......................................... 424/263

[56] References Cited
PUBLICATIONS

Chem. Abst., 74-88047g (1971).

*Primary Examiner*—Stanley J. Friedman
*Attorney, Agent, or Firm*—Hammond & Littell

[57] ABSTRACT

Pharmaceutical compositions containing as an active ingredient a compound of the formula

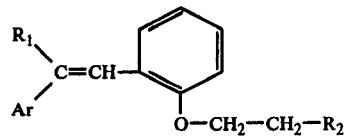

wherein
 $R_1$ is hydrogen or methyl,
 Ar is phenyl, 2-pyridyl, 6-methyl-2-pyridyl, 2-quinolyl, 1-methyl-benzimidazol-2-yl, 2-pyrazinyl or 3-methyl-isoxazol-5-yl, and
 $R_2$ is dimethylamino, monomethylamino or morpholino, or a non-toxic, pharmaceutically acceptable acid addition salt thereof; and a method of using the same as antiarrhythmics.

4 Claims, No Drawings

ANTIARRHYTHMIC METHOD OF USE

This invention relates to pharmaceutical dosage unit compositions containing certain β-aryl-2-aminoethoxy-styrols or non-toxic acid addition salts thereof, as well as to a method of using the same as antiarrhythmics.

The Prior Art

German Offenlegungsschrift No. 1,939,809 discloses a genus of β-aryl-2-aminoalkoxy-styrols of the formula

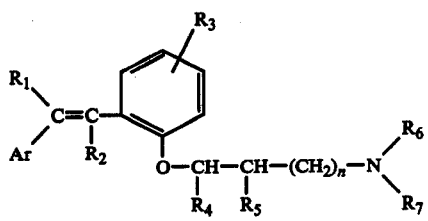

wherein

Ar is phenyl; 2-,3- or 4-pyridyl, which may optionally be lower alkyl-substituted; 2-quinolyl or 2-pyrazinyl, each of which may optionally be lower alkyl-substituted; pyrimidyl which may optionally be lower alkyl-substituted; 2-benzimidazolyl which may optionally be halo-, lower alkyl- or trifluoromethyl-substituted; 2-furyl; 2-thienyl; 5-isoxazolyl which may optionally be lower alkyl - or phenyl-substituted; or 5-(1,2,4-oxadiazolyl) which may optionally be lower alkyl-substituted;

$R_1$, $R_2$, $R_4$ and $R_5$, which may be identical to or different from each other, are each hydrogen or lower alkyl;

$R_3$ is hydrogen or lower alkoxy;

$R_6$ and $R_7$, which may be identical to or different from each other, are each hydrogen, lower alkyl, alkenyl, hydroxy-alkyl, alkoxyalkyl, axralkyl or, together with each other and the nitrogen to which they are attached, a monocyclic saturated heterocyclic 5 - to 7 - membered ring which may optionally be interrupted by an oxygen or an additional nitrogen; and n is 0 or 1;

and non-toxic, pharmaceutically acceptable acid addition salts thereof. These compounds are disclosed to have primarily analgesic properties, and some of them are said to possess also sedative and muscle-relaxing properties.

The German publication further discloses that these compounds may be incorporated as active ingredients into conventional pharmaceutical dosage unit compositions, such as tablets, coated pills, suppositories and the like, the single effective dosage range for adults being from 5 to 100 mgm, preferably 20 to 50 mgm.

DESCRIPTION OF THE INVENTION

We have discovered that a certain sub-genus of compounds within the genus disclosed in the said German Offenlegungsschrift, namely the β-aryl-2-aminoethoxy-styrols of the formula

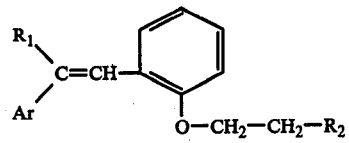

wherein $R_1$ is hydrogen or methyl,

Ar is phenyl, 2-pyridyl, 6-methyl-2-pyridyl, 2-quinolyl, 1-methyl-benzimidazol-2-yl, 2-pyrazinyl or 3-methyl-isoxazol-5-yl, and $R_2$ is dimethylamino, monomethylamino or morpholino, and non-toxic, pharmaceutically acceptable acid addition salts thereof, have very effective antiarrhythmic properties and very low toxicities in comparison to the therapeutic dosage range.

Thus, the present invention relates to novel antiarrhythmic pharmaceutical compositions containing as an active ingredient a compound of the formual I above or a non-toxic, pharmaceutically acceptable acid addition salt thereof, as well as to a method of relieving cardiac arrhythmia therewith.

The compounds embraced by formula I may be prepared by the following methods:

Method A

By reacting a styrol of the formual

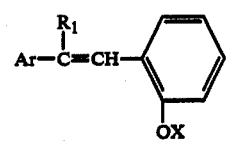

wherein

Ar and $R_1$ have the same meanings a in formula I, and

X is hydrogen or acetyl, with an amine of the formula

$$Y-CH_2-CH_2-R_2 \qquad (III)$$

wherein $R_2$ has the same meanings as in formula I, and

Y is halogen, in the presence of base.

The reaction is carried out in an inert solvent, such as benzene, chlorobenzene, toluene or xylene, and at elevated temperatures, preferably at the boiling point of the particular solvent which is used. Alkali metal hydroxides or carbonates, but preferably alkali metal alcoholates are used as the base.

Method B

By reacting a compound of the formula

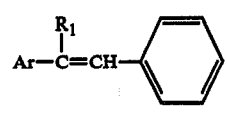

wherein

Ar and $R_1$ have the same meanings as in formula I, and

Z is a substituent which is exchangeable for a basic substituent, such as halogen or tosyl, with an amine of the formula $$H-R_2 \quad (V)$$

wherein $R_2$ has the same meanings as in formula I.

The reaction is carried out in a solvent in the presence of an acid-binding agent. Suitable acid-binding agents are inorganic or organic bases, or an excess of the amine of the formula V may be used, and the latter may at the same time serve as a solvent. The reaction is carried out at elevated temperatures, generally at temperatures between 60° and 120° C. If a readily volatile amine of the formula V is used, the reaction is appropriately carried out in a closed vessel.

The compounds of the formula I may be converted in the usual way into their acid addition salts by means of inorganic or organic acids. If Ar is a heterocycle containing nitrogen, it is possible by stepwise neutralization to add a proton only to the nitrogen atom of the basic side-chain. If an excess of acid is used, salt formation is also effected with inclusion of the nitrogen atoms of the heterocyclic rings. Examples of non-toxic pharmaceutically acceptable acid addition salts are those formed with hydrochloric acid, hydrobromic acid, sulfuric acid, phosphoric acid, tartaric acid, p-toluenesulfonic acid, 8-chlorotheophylline or the like.

The compounds of the formula II used as starting compounds for method A may be prepared according to known processes (cf. L. Horwitz, J. Org. Chem. 21, 1039-1041 [1956]). The compounds of the formula III are described in the literature or may be prepared in analogy to methods described in the literature.

The starting compounds of the formula IV for method B may, for example, be prepared by reaction of a corresponding 2-(2-acetoxystyryl)-aryl with a benzenesulfonic acid-2-halo-ethyl ester in the presence of potassium methoxide in toluene. For example, the following starting compounds were prepared in this manner:

2-[2-(2-Chloroethoxy)styryl]-pyridine, m.p. 57°-59° C., and

2-[2-(2-Chloroethoxy)styryl]-quinoline, m.p. of the hydrochloride 200°-202° C.

The following examples illustrate the preparation of compounds of the formula I.

EXAMPLE 1

2-[o-(β-Dimethylamino-ethoxy)-styryl]-pyridine and acid addition salts thereof by method A.

A solution of 400 gm of 2-(2-acetoxy-styryl)-pyridine in 1250 ml of chlorobenzene was admixed with 235.5 gm of potassium methylate and the mixture was heated to 110° C. while stirring, whereby a yellow suspension was obtained. 483 gm of dimethylaminoethyl chloride-hydrochloride were shaken with 1000 ml of ice-cold aqueous 30% sodium hydroxide in a shaking funnel, and the liberated oily base was separated and added dropwise to the suspension in 6 equal portions, each over a period of 15 minutes; the not yet needed amount of dimethylaminoethyl chloride was kept at 0° C. in order to avoid premature self-reaction. The resulting mixture was stirred at 110° C. for 30 minutes, cooled and admixed with ice. After extraction of the solvent, an oil remained which was distilled in vacuo; b.p. 156°-161° C. at 0.06 mm Hg. 376 gm of a honey-colored oil were obtained. Yield: 83.9% of theory of 2-[o-(β-dimethylamino-ethoxy)-styryl]-pyridine.

123 gm of the oily reaction product thus obtained were dissolved in a mixture of 750 ml of ethyl acetate and 330 ml of absolute ethanol. 430 ml of a solution of 132 ml of ethanolic hydrochloric acid (12.72%; weight-/volume) in 638 ml of ethyl acetate were gradually added, while stirring vigorously and taking care that the mixture did not turn yellow. Then, 600 ml of ethyl acetate were added, and the mixture was cooled to 0° C. The precipitated crystals were collected by suction filtration, washed with ethyl acetate and dried over concentrated sulfuric acid and potassium hydroxide in a desiccator, yielding 93 gm of the monohydrochloride of the formula

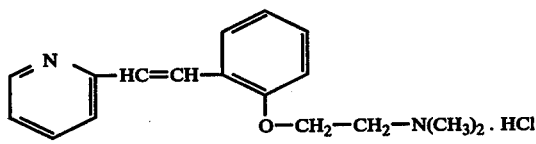

which had a melting point of 186°-187.5° C.

When an excess of ethanolic hydrochloric acid was used, that is, a total of 300 ml of the hydrochloric acid of the above concentration, the solution turned deep yellow, and the dihydrochloride of 2-[o-(β-dimethylamino-ethoxy)-styryl]-pyridine, m.p. 218°-220° C., was obtained.

For the preparation of the p-toluenesulfonate, 2.68 gm of the free 2-[o-(β-dimethylamino-ethoxy-styryl]-pyridine base were dissolved in 20 ml of absolute ethyl acetate, and 19 ml of a solution of 1.72 gm of p-toluenesulfonic acid in 20 ml of ethyl acetate were slowly added while stirring. After cooling on ice, the mono-p-toluenesulfonate crystallized out, which was washed with ethyl acetate and dried over sulfuric acid in a desiccator. M.p.: 128°-130° C.; yield 3.1 gm.

For the preparation of the phosphate, 2.68 gm of the free 2-[o-β-dimethylamino-ethoxy)-styryl]-pyridine base were dissolved in 40 ml of ethanol and a solution of 0.346 gm of 85% phosphoric acid was slowly added dropwise while stirring. The colorless solution was evaporated to 25 ml, 25 ml of ethyl acetate were added, and the mixture was put into an ice bath. After one hour a white precipitate of the phosphate of the above base crystallized out. Pursuant to analysis, 1 mol of base combined with ½ mol of phosphoric acid. M.p.: 133°-134° C; yield 1.1 gm.

The 2-(o-acetoxy-styryl)-pyridine (b.p. 162°-175° C. at 0.06 mm Hg) used as starting material was prepared from 2-picoline and salicylaldehyde in the presence of acetic acid anhydride at 170° C.

Using a procedure analogous to that described in Example 1, the following compounds of the formula I were also prepared.

EXAMPLE 2

1-[o-(β-Dimethylamino-ethoxy)]-phenyl-2-(pyridyl-2')-propene-1 was prepared from 1-(o-acetoxy-phenyl)-2-(pyridyl-2')-propene-1 (b.p. 140° C. at 0.05 mm Hg) and dimethylamino-ethyl chloride, and the free base was converted into its monohydrochloride, yielding 85% of theory of the compound of the formula

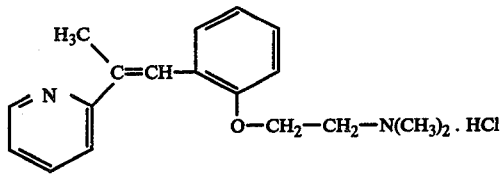

which had a melting point of 128°–133° C.

EXAMPLE 3

2-[o-(β-Dimethylamino-ethoxy)-styryl]-quinoline was prepared from 2-(o-hydroxy-styryl)-quinoline (m.p. 274°–278° C.) and dimethylamino-ethyl chloride, and the free base was converted into its monohydrochloride, yielding 86% of theory of the compound of the formula

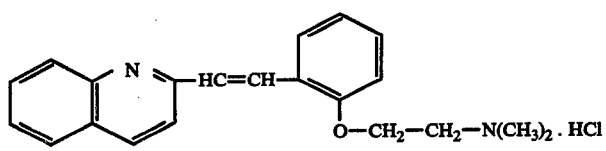

which had a melting point of 188° C.

EXAMPLE 4

2-[o-(β-Methylamino-ethoxy)-styryl]-pyridine and its monohydrochloride by method B.

16 gm of 2-[o-(β-chloro-ethoxy)-styryl]-pyridine (m.p. 57°–59° C.) were dissolved in 50 ml of methanol, the solution was mixed at −15° C. with 120 ml of liquid methylamine freshly removed from a bomb, and the mixture was heated at 80° C. in an autoclave for 4 hours. After cooling and releasing the pressure, the contents of the autoclave were evaporated, the residue was dissolved in dilute acetic acid, and the solution was extracted twice with ether to remove weakly basic products. Then, the aqueous phase was made alkaline with 2 N sodium hydroxide solution and was extracted with ethyl acetate. After drying the ethyl acetate extract with sodium sulfate and distilling off the solvent, an oily residue was obtained which crystallized after standing overnight. 13.6 gm (88.2% of theory) of 2-[o-(β-methylaminoethoxy)-styryl]-pyridine were obtained.

The free base thus obtained was dissolved in 200 ml of acetone, the solution was filtered with charcoal and then admixed with 20 ml of ethanol. A solution of 15.3 ml of ethanolic 12.72% hydrochloric acid (weight-/volume) in 50 ml of acetone was carefully added until the mixture began to turn yellow, which required about 59 ml of the acidic precipitation solution. Ether was then added until the mixture began to become turbid, whereupon it was stirred while cooling in an ice bath. Within 1 hour a pale yellow substance crystallized out, which was collected by suction filtration and dried in a desiccator. 9.3 gm (52% of theory) of the compound of the formula

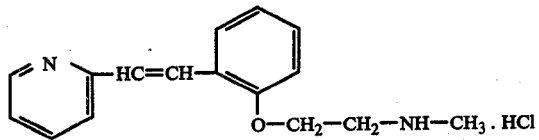

were obtained, which had a melting point of 178°–180° C.

The required starting compound, 2-[o-β-chloroethoxy)-styryl]-pyridine (m.p. 57°–59° C.), was prepared from 2-(o-acetoxy-styryl)-pyridine and benzenesulfonic acid β-chloroethyl ester in the presence of potassium methylate in toluene.

Using a procedure analogous to that described in Example 4, the following compounds of the formula I were also prepared:

EXAMPLE 5

2-[o-(β-Morpholino-ethoxy)-styryl]-pyridine was prepared from 2-[o-(β-chloro-ethoxy)-styryl]-pyridine (m.p. 57°–58° C.) and morpholine, and the free base was converted into its dihydrochloride, yielding 53% of theory of the compound of the formula

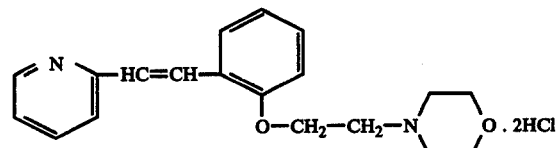

which had a melting point of 248° C.

EXAMPLE 6

2-[o-(β-Dimethylamino-ethoxy)-styryl]-6-methyl-pyridine was prepared from 2-[o-(β-chloro-ethoxy)-styryl]-6-methyl-pyridine and dimethylamine, and the free base was converted into its monohydrochloride, yielding 45% of theory of the compound of the formula

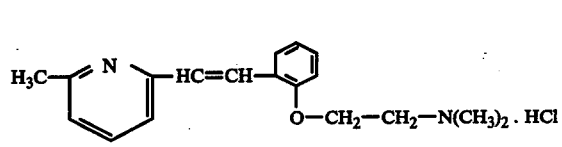

which had a melting point of 200° C.

EXAMPLE 7

2-[o-(β-Dimethylamino-ethoxy)-styryl]-1-methyl-benzimidazole was prepared from 2-[o-(β-chloro-ethoxy)-styryl]-1-methyl-benzimidazole and dimethylamine, and the free base was converted into its dihydrochloride, yielding 18% of theory of the compound of the formula

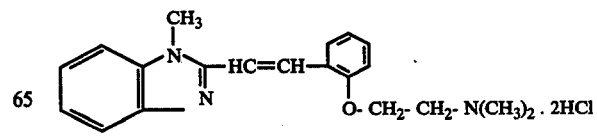

which had a melting point of 208° C.

EXAMPLE 8

2-[o-(β-Dimethylamino-ethoxy)-styryl]-pyrazine was prepared from 2-[o-(β-chloro-ethoxy)styryl]-pyrazine and dimethylamine, and the free base was converted into its monohydrochloride, yielding 54% of theory of the compound of the formula

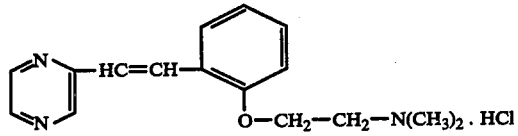

which had a melting point of 194°–195° C.

EXAMPLE 9

2-(β-Dimethylamino-ethoxy)-stilbene was prepared from 2-(β-chloro-ethoxy)-stilbene and dimethylamine, and the free base was converted into its hydrochloride, yielding 45% of theory of the compound of the formula

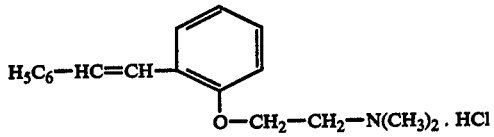

which had a melting point of 199° C.

EXAMPLE 10

5-[o-(β-Dimethylamino-ethoxy)-styryl]-3-methyl-isoxazole was prepared from 2-[o-(β-chloro-ethoxy)-styryl]-3-methyl-isoxazole and dimethylamine, and the free base was converted into its hydrochloride, yielding 22% of theory of the compound of the formula

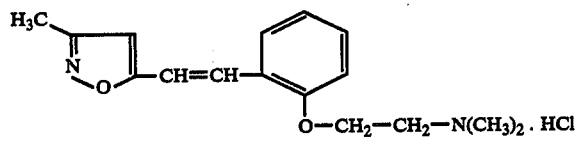

which had a melting point of 150°–151° C.

The antiarrhythmic activity of the compounds of the formula I and their non-toxic acid addition salts was ascertained on isolated guinea pig auricles, on anesthetized dogs and on mice by the methods described below, and in the following paragraphs the test results for a few representative species of the genus are given, where

| | |
|---|---|
| 2-[o-(β-Dimethylamino-ethoxy)-styryl]-pyridine monohydrochloride | = A, |
| 2-[o-(β-Methylamino-ethoxy)-styryl]-pyridine dihydrochloride | = B. |
| 2-[o-(β-Morpholino-ethoxy)-styryl]-pyridine dihydrochloride | = C, |
| 1-[o-(β-Dimethylamino-ethoxy)-phenyl]-2-(pyridyl-2)-propene-1 monohydrochloride | = D, |
| 2-[o-(β-Dimethylamino-ethoxy)-styryl]-6-methyl-pyridine hydrochloride | = E, |
| 2-[o-(β-Dimethylamino-ethoxy)-styryl]-quinoline hydrochloride | = F, |
| 2-[o-(β-Dimethylamino-ethoxy)-styryl]-1-methyl-benzimidazole dihydrochloride | = G, |
| 2-[o-(β-Dimethylamino-ethoxy)-styryl]-pyrazine | = H, |
| 2-(2-Dimethylamino-ethoxy)-stilbene hydrochloride | = I, |
| and 5-[2-(2-Dimethylamino-ethoxy)-styryl]-3-methyl-isoxazole hydrochloride | = J. |

1. Reduction of the maximum driving frequency of isolated auricles of guinea pigs The tests were carried out using an adaption of the method of DAWES (Brit. J. Pharmacol.1, 90, 1946). Guinea pigs of both sexes, body weight between 300 and 400 gm were killed by a blow on the neck. The left auricles were quickly removed and put into an organ bath of 100 ml. The organ bath was filled with tyrode solution, which was infused with a mixture of 98% of oxygen and 2% of carbon dioxide. The mixture had a temperature of 37° C. and a pH-value of 7.4.

The auricles were stimulated with square wave impulses of 1 millisecond duration at a voltage 200% higher than the threshold voltage and a frequency of 1 Hz (Hugo Sachs, Stimulator II). A weight of 0.4 gm was applied to the auricles and the contractions were continuously measured isometrically by means of a force displacement transducer (Grass Ft 03) and recorded on a Grass polygraph (model 5). After sufficient equilibration time (15 min.) the stimulation rate was increased every 10 seconds by 1 Hz until the maximum driving frequency (MDF) was reached. The MDF is defined as the stimulation frequency, where every stimulation is still answered by a contraction. The MDF was determined before and 5 and 10 minutes after adding the test compound. The test compound was added cumulatively to the organ bath. The concentration causing a 50% decrease of the MDF ($EC_{50}$) was calculated from a dose-response curve. The results are shown in the following table:

| Compound | $EC_{50}$ (gm/ml) |
|---|---|
| A | $3.8 \times 10^{-6}$ |
| B | $8.3 \times 10^{-6}$ |
| C | $3.3 \times 10^{-5}$ |
| D | $3.1 \times 10^{-6}$ |
| E | $6.3 \times 10^{-6}$ |
| F | $1.0 \times 10^{-5}$ |
| G | $9.0 \times 10^{-6}$ |
| H | $2.5 \times 10^{-5}$ |
| I | $1.0 \times 10^{-5}$ |
| J | |

2. Prevention of ventricular arrhythmia provoked by adrenalin in dogs under halothane anesthesia According to the method described by ALLEN, et al in Brit. J. Pharmacol. 45, 561 (1972), dogs were anesthetized by subcutaneous injection of 0.5 mgm/kg morphine sulfate and by intravenous injection of 20 mg/kg pentobarbitone. The animals were given artificial respiration with room air from a Starling pump via a cuffed endotracheal tube. The electrocardiogram (lead II) was recorded on a Devices recorder (Type M 8 or M 4). The test compound was injected through a polyethylene catheter inserted into a foreleg vein.

Observations were made on 4 dogs. The artificial respiration was continued adding 1% halothane to the room air. 15 minutes later adrenalin was injected at doses of 0.2 and increased to 0.4, 0.8, 1.2, 1.6, 2.0, 2.4 and 2.8 mg/kg intravenously, at intervals of 7 to 10 minutes between each dose, until ventricular tachycardia had been produced. After the arrhythmia-producing dose of adrenalin had been established, compound A was injected intravenously. 5 minutes later the adrenalin injection was repeated, using the same dose. The dose of the test compound was increased to obtain the minimum dose which prevented the adrenalin-induced arrhythmia. It was found that the mean dose of substance A that abolished the adrenalin arrhythmias in 4 dogs was 0.18 ± 0.04 mgm/kg i.v.

3. Suppression of ouabain-induced ventricular arrhythmia in dogs

According to the method described by ALLEN, et al. (supra), dogs were anesthetized by subcutaneous injection of morphine sulfate (0.5 mgm/kg), followed by intravenous injection of pentobarbitone (20 mgm/kg). The animals were given artificial respiration with room air from a Starling pump via a cuffed endotracheal tube. The electrocardiogram (lead II) was recorded on a Devices recorder (Type M8 or M 4). Test compound administration was through a polyethylene catheter inserted in a foreleg vein.

Observations were made on 12 dogs. Ventricular tachycardia was produced by intravenous injection of ouabain, first 40 mgm/kg, followed after 30 minutes by 20 mgm/kg and by 10 mgm/kg every 15 minutes until ventricular tachycardia was established. 10 minutes after the last ouabain injection, the test compound was continuously infused intravenously from a motor-driven syringe at a rate of 0.2 mgm/kg per minute, until sinus rhythm returned. The mean dose of ouabain to produce ventricular tachycardia was 60 ± 2.8 mg/kg. The mean dose of compound A required to convert the ventricular tachycardia to sinus rhythm was 0.76 ± 0.18 mg/kg i.v.

4. Acute i.v. toxicity in mice

Mice of both sexes having a body weight of 20 to 25 gm were used. The test compound was dissolved in distilled water and injected into the mice with a volume of 0.1 ml/10 gm body weight by way of a tail vein. Each dose was injected into 10 mice. The number of dead animals was determined and the median lethal dose ($LD_{50}$) was calculated using the method of LITCHFIELD and WILCOXON [J. Pharmac. Exp. Ther. 96, 99 (1949)]. The $LD_{50}$ for compound A was 25 (23.8–26.3) mgm/kg i.v.

Thus in experiments performed on isolated auricles by means of a well-established method for testing antiarrhythmic compounds all test compounds showed a similar antiarrhythmic activity in reducing the maximum driving frequency. The more complex, but also more specific, tests on anesthetized dogs confirmed the finding that, for example, compound A is a very effective antiarrhythmic compound.

The lowest therapeutic dose was 0.1 mgm/kg i.v., which is about 100 to 200 times smaller than the mean toxic dose. Therefore, an excellent therapeutic ratio for compound A is given.

For pharmaceutical purposes the compounds embraced by formula I or their non-toxic acid addition salts are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups and the like. A single effective antiarrhythmic oral dosage unit of the compounds of this invention is from 2.0 to 4.2 mgm/kg body weight, preferably from 2.5 to 3.4 mgm/kg body weight, and the daily dose rate is from 5.0 to 12.5 mgm/kg body weight. A single effective antiarrhythmic intravenous dosage unit is from 0.1 to 0.5 mgm/kg body weight, preferably 0.2 to 0.25 mgm/kg body weight, and the daily dose rate is from 0.33 to 1.67 mgm/kg body weight.

The following examples illustrate a few pharmaceutical dosage unit compositions comprising a compound of the formula I or a non-toxic salt thereof as an active ingredient and represent the best modes contemplated of putting the invention into practical use. The parts are parts by weight unless otherwise specified.

EXAMPLE 11

Tablets

The tablet composition is compounded from the following ingredients:

| | |
|---|---:|
| 2-[o-($\beta$-Dimethylamino-ethoxy)-styryl]-pyridine monohydrochloride | 150.0 parts |
| Lactose | 130.0 parts |
| Corn starch | 63.0 parts |
| Cellulose, microcrystalline | 50.0 parts |
| Polyvinyl pyrrolidone | 5.0 parts |
| Magnesium stearate | 2.0 parts |
| Total | 400.0 parts |

Preparation

The pyridine compound is intimately admixed with the lactose, the cellulose and the corn starch, the mixture is moistened with an aqueous 10% solution of the polyvinyl pyrrolidone, and the moist mass is granulated by passing it through a fine-mesh screen. The granulate is dried at 45° C. and admixed with the magnesium stearate, and the resulting composition is compressed into 400 mgm-tablets in a conventional tablet making machine. Each tablet contains 150 mgm of the pyridine compound and is an oral antiarrhythmic dosage unit composition.

EXAMPLE 12

Coated pills

The pill core composition is compounded from the following ingredients:

| | |
|---|---:|
| 2-[o-($\beta$-Dimethylamino-ethoxy)-styryl]-pyridine monohydrochloride | 150.0 parts |
| Lactose | 130.0 parts |
| Corn starch | 63.0 parts |
| Cellulose, microcrystalline | 50.0 parts |
| Polyvinyl pyrrolidone | 5.0 parts |
| Magnesium stearate | 2.0 parts |
| Total | 400.0 parts |

Preparation:

The ingredients are compounded and granulated in the same manner as in the preceding example, and the composition is compressed into 400 mgm-pill cores which are subsequently insulated with an enthanolic 15% solution of the polyvinyl pyrrolidone and finally sugar-coated in conventional manner. Each coated pill contains 150 mgm of the pyridine compound and is an oral antiarrhythmic dosage unit composition.

EXAMPLE 13

Gelatin capsules

The capsule filler composition is compounded from the following ingredients:

| | |
|---|---:|
| 2-[o-($\beta$-Dimethylamino-ethoxy)-styryl]-pyridine monohydrochloride | 150.0 parts |
| Corn starch, dry | 147.0 parts |

-continued

| | |
|---|---|
| Colloidal silicic acid | 3.0 parts |
| Total | 300.0 parts |

Preparation:

The ingredients are intimately admixed, the mixture is passed through a 0.75 mm-mesh screen, and 300 mgm-portions of the screened mixture are filled into No. 1 gelatine capsules. Each capsule contains 150 mgm of the pyridine compound and is an oral antiarrhythmic dosage unit composition.

EXAMPLE 14

Dry Ampules (a) The contents of the dry ampule are prepared from the following ingredients:

| | |
|---|---|
| 2-[o-($\beta$-Dimethylamino-ethoxy)-styryl]-pyridine monohydrochloride | 15.0 parts |
| Double-distilled water q.s.ad | 1000.0 parts by vol. |

Preparation:

The pyridine compound is dissolved in the distilled water, the solution is filtered through a membrane filter, and 1 cc-portions of the filtrate are filled into sterilized brown 2cc-ampules. The solution is then frozen and lyophilized under aseptic conditions in the ampules, and the ampules are finally sealed.

(b) Solution ampules

The contents of the solution ampules are compounded from the following ingredients:

| | |
|---|---|
| Citric acid · H$_2$O | 1.0 parts |
| Sodium acid phosphate with 12 mols of water of crystallization | 20.0 parts |
| Sodium chloride | 6.0 parts |
| Double-distilled water q.s.ad | 1000.0 parts by vol. |

Preparation:

The solid components are successively dissolved in the distilled water, the solution is filtered through a membrane filter, and the filtrate is filled into a sterilized brown 1cc-ampules which are then heated at 120° C. for 20 minutes in an autoclave and thereafter sealed.

Just prior to use, the solution is withdrawn from the solution ampule with a syringe and injected into the dry ampule, whereby an injectable antiarrhythmic solution containing 15 mgm of the pyridine compound is obtained.

Any one of the other compounds embraced by formula I or a non-toxic, pharmaceutically acceptable acid addition salt may be substituted for the particular active ingredient in Examples 11 through 14. Likewise, the amount of active ingredient in these illustrative examples may be varied to achieve the dosage unit ranges set forth above, and the amounts and nature of the inert pharmaceutical carrier ingredients may be varied to meet particular requirements.

While the present invention has been illustrated with the acid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of alleviating cardiac arrhythmia in a warm-blooded animal, which comprises perorally or parenterally administering to said animal an effective antiarrhythmic amount of a compound of the formula

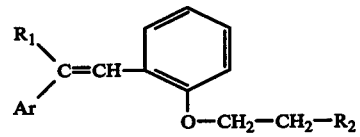

wherein $R_1$ is hydrogen or methyl,

Ar is 2-pyridyl or 6-methyl-2-pyridyl, and $R_2$ is dimethylamino or monomethylamino or a non-toxic, pharmaceutically acceptable acid addition salt thereof.

2. The method of claim 1, where said compound is 2-[o-($\beta$-dimethylamino-ethoxy)-styryl]-pyridine or a non-toxic, pharmaceutically acceptable acid addition salt thereof.

3. The method of claim 1, where said compound is administered perorally at a dosage of 2.0 to 4.2 mgm/kg body weight.

4. The method of claim 1, where said compound is administered intravenously at a dosage of 0.1 to 0.34 mgm/kg body weight.

* * * * *